United States Patent [19]
Oda et al.

[11] Patent Number: 5,955,639
[45] Date of Patent: Sep. 21, 1999

[54] ETHYLENE/ALPHA-OLEFIN COPOLYMER

[75] Inventors: Hidekuni Oda, Iwakuni; Tatuo Kinoshita, Yamaguchi-ken; Akiyoshi Shimizu, Iwakuni, all of Japan

[73] Assignee: Mitsui Chemicals, Inc., Tokyo, Japan

[21] Appl. No.: 08/098,236

[22] Filed: Jul. 29, 1993

Related U.S. Application Data

[63] Continuation of application No. 07/813,043, Dec. 23, 1991, abandoned, which is a continuation of application No. 07/567,709, Aug. 14, 1990, abandoned, which is a continuation of application No. 07/364,535, Jun. 12, 1989, abandoned, which is a continuation of application No. 07/220,954, Jun. 23, 1988, abandoned, which is a continuation of application No. 06/885,399, Jul. 18, 1986, abandoned, which is a continuation of application No. 06/770,019, Aug. 29, 1985, abandoned, which is a continuation of application No. 06/553,873, Nov. 21, 1983, abandoned, which is a continuation of application No. 06/338,138, Jan. 8, 1982, abandoned.

[30] Foreign Application Priority Data

Jan. 13, 1981 [JP] Japan ..................................... 56-2603
Jan. 13, 1981 [JP] Japan ..................................... 56-2604

[51] Int. Cl.[6] ...................................................... C10L 1/16
[52] U.S. Cl. ................... 585/10; 585/12; 585/20
[58] Field of Search ................... 585/10, 12, 20

[56] References Cited

U.S. PATENT DOCUMENTS

| | | | |
|---|---|---|---|
| 3,522,180 | 7/1970 | Sweeney et al. | 55/12 |
| 3,600,311 | 8/1971 | Naiman et al. | 585/10 |
| 3,676,521 | 7/1972 | Stearns et al. | 585/18 |
| 3,679,380 | 7/1972 | Biswell et al. | 585/12 |
| 3,697,429 | 10/1972 | Engel et al. | 585/12 |
| 3,851,011 | 11/1974 | Stearns et al. | 260/683 |
| 3,897,353 | 7/1975 | Morduchowitz et al. | 585/10 |
| 3,923,919 | 12/1975 | Stearns et al. | 585/18 |
| 4,022,590 | 5/1977 | Morduchowitz | 585/10 |
| 4,069,166 | 1/1978 | Masunaga et al. | 585/12 |
| 4,182,922 | 1/1980 | Schick et al. | 585/18 |

FOREIGN PATENT DOCUMENTS

| | | |
|---|---|---|
| 924462 | 3/1946 | France . |
| 1559920 | 3/1968 | France . |

*Primary Examiner*—Walter D. Griffin
*Assistant Examiner*—Nadine Preisch
*Attorney, Agent, or Firm*—Sherman and Shalloway

[57] ABSTRACT

A copolymer of ethylene and an alpha-olefin having an ethylene content of from 30 to 90 mole %, a number average molecular weight of from 300 to 30,000 and a molecular weight distribution defined by a Q value (the ratio of the weight average molecular weight to the number average molecular weight) of not more than 3 and a Z value (the ratio of the maximum value of the molecular weight to the minimum value of the molecular weight when the molecular weight is measured by gel permeation chromatography) of from 15 to 200. The said copolymer can be produced by a process comprising copolymerizing ethylene with an alpha-olefin in the liquid phase in the presence of a polymerization catalyst composed of a combination of a soluble vanadium compound and an organoaluminum compound in the co-presence of hydrogen, characterized in that (a) the copolymerization is carried out in a continuous manner,
(b) the concentration of the vanadium compound in the polymerization system is maintained at 0.3 to 30 millimoles/liter, and
(c) the vanadium compound is supplied to the polymerization system as a solution in a polymerization medium in a concentration which is 1 to 5 times the concentration of the vanadium compound in the liquid phase. This compound is useful as a synthetic lubricant oil, a fuel oil additive and a lubricant oil additive.

20 Claims, No Drawings

ETHYLENE/ALPHA-OLEFIN COPOLYMER

This application is a continuation of application Ser. No. 07/813,043 now abandoned, filed Dec. 23, 1991; which is a continuation of application Ser. No. 07/567,709 now abandoned, filed Aug. 14, 1990; which is a continuation of application Ser. No. 07/364,535 now abandoned, filed Jun. 12, 1989; which is a continuation of application Ser. No. 07/220,954 now abandoned, filed Jun. 23, 1988; which is a continuation of application Ser. No. 06/885,399 now abandoned, filed Jul. 18, 1986; which is a continuation of application Ser. No. 06/770,019 now abandoned, filed Aug. 29, 1985; which is a continuation of application Ser. No. 06/553,873 now abandoned, filed Nov. 21, 1983; which is a continuation of application Ser. No. 06/338,138 now abandoned, filed Jan. 8, 1982.

This invention relates to a novel ethylene/alpha-olefin copolymer. More specifically, it relates to an ethylene/alpha-olefin copolymer having a low molecular weight and a relatively narrow molecular weight distribution, a process for its production, and its use as a synthetic lubricant oil, a fuel oil additive and a lubricant oil additive.

It is known that an ethylene/alpha-olefin co-polymer having a low molecular weight which is useful as a synthetic lube oil is obtained by copolymerizing ethylene with an alpha-olefin having at least 3 carbon atoms in the liquid phase in the presence of a catalyst composed of a combination of a soluble vanadium compound and an organoaluminum compound in the co-presence of hydrogen (see U.S. Pat. No. 3,851,011). When the copolymer is produced by the method specifically disclosed in the Example of this U.S. Patent, it has poor uniformity (namely, it has broad molecular weight and composition distributions and sometimes it is obtained as a milky liquid or a white paste). When the product obtained has a low viscosity, it does not have a high flash point as a lubricant oil unless a low-molecular-weight portion is removed. On the other hand, if a product having a high viscosity is obtained, it has an excessively high pour point and is not practical as a lube oil. Oils which have a viscosity at 100° C. of at least 60 centistokes are useful as lube oils for high loads. Those copolymers which are disclosed in the above Patent and have a viscosity in this range have too high a pour point to be used for practical applications. The U.S. Patent suggests that the copolymer can be fractionally distilled, and that a product having a narrow boiling point range obtained by fractional distillation can remove the aforesaid defects with regard to pour points and flash points. It is extremely difficult in this case, however, to obtain a product having a satisfactorily high viscosity index.

Japanese Patent Publications Nos. 37237/1975 and 7717/1976 suggest processes for producing an ethylene/alpha-olefin copolymer having a low molecular weight, and state that the production of copolymers having a narrow molecular weight distribution is possible. These processes, however, have the defect that special compounds must be used as a molecular weight controlling agent or a catalyst promotor. In addition, copolymers having a sufficiently low molecular weight, such as those of lubricant oil grade, which are prepared in accordance with the specific disclosures of these Patent Publications do not have a sufficiently narrow distribution of molecular weight, and, therefore, have the same defects as described above with regard to U.S. Pat. No. 3,851,011.

It is an object of this invention therefore to provide an ethylene/alpha-olefin copolymer having a narrow molecular weight distribution.

Another object of this invention is to provide a process for producing the aforesaid copolymer in a continuous manner.

Still another object of this invention is to provide a synthetic lubricant oil having a low evaporation loss, a high flash point, excellent low-temperature flowability, good shear stability, good oiliness, and a high viscosity index.

Yet another object of this invention is to provide a fuel oil having excellent low-temperature flowability.

Other objects and advantages of this invention will become apparent from the following detailed description.

According to one aspect of this invention, there is provided a copolymer of ethylene and an alpha-olefin having an ethylene content of from 30 to 90 mole %, a number average molecular weight of from 300 to 30,000, and a molecular weight distribution defined by a Q value (the ratio of the weight average molecular weight to the number average molecular weight) of not more than 3 and a Z value (the ratio of the maximum value of the molecular weight to the minimum value of the molecular weight when the molecular weight is measured by gel-permeation chromatography) of from 15 to 200.

According to another aspect of this invention, the ethylene/alpha-olefin copolymer can be produced advantageously by a process which comprises copolymerizing ethylene with an alpha-olefin in the liquid phase in the presence of a polymerization catalyst composed of a combination of a soluble vanadium compound and an organoaluminum compound in the co-presence of hydrogen, characterized in that (a) the copolymerization is carried out in a continuous manner, (b) the concentration of the vanadium compound in the polymerization system is maintained at 0.3 to 30 millimoles/liter, and (c) the vanadium compound is supplied to the polymerization system as a solution in a polymerization medium at a concentration which is 1 to 5 times the concentration of the vanadium compound in the liquid phase.

The soluble vanadium compound used as one component of the polymerization catalyst in the above process is a vanadium-containing compound which is soluble at least partly, and in practice, mostly, in the polymerization medium used. Generally, it includes compounds of the following formula

  (I-1)

and

  (I-2)

wherein $R^1$ represents an aliphatic hydrocarbon group having 1 to 20 carbon atoms, preferably 1 to 10 carbon atoms, $X^1$ represents a halogen atom, and n is a number of from 0 to 3.

The aliphatic hydrocarbon group $R^1$ in formula (I-1) is a linear or branched alkyl group, such as methyl, ethyl, n-propyl, isopropyl, n-butyl, iso-butyl, sec-butyl, n-pentyl, iso-pentyl, n-hexyl, iso-hexyl, heptyl, octyl, nonyl, decyl, dodecyl, tetradecyl, pentadecyl, heptadecyl, octadecyl, nonadecyl, and eicosyl. Those having 1 to 10 carbon atoms are preferred.

Chlorine and bromine are preferred as the halogen atom $X^1$.

Specific examples of the vanadium compound are given below. $VOCl_3$, $VO(OCH_3)Cl_2$, $VO(OCH_3)_2Cl$, VO (OCH₃)₃, VO(OC₂H₅)Cl₂, VO(OC₂H₅)₁.₅Cl₁.₅, VO(OC₂H₅)₂Cl, VO(OC₂H₅)₃, VO(OC₂H₅)₁.₅Br₁.₅, VO(OC₃H₇)₂Cl, VO(OC₃H₇)₁.₅Cl₁.₅, VO(OC₃H₇)₂Cl, VO(OC₃H₇)₃, VO(On-C₄H₉)Cl₂, VO(On-C₄H₉)₂Cl, VO(Oiso-C₄H₉)Cl₂, VO(Osec-C₄H₉)₃, VO(OC₅H₁₁)₁.₅Cl₁.₅, VO(Oiso-C₅H₁₁)₂Cl, VO(Oiso-C₅H₁₁)₁.₅Cl₁.₅, VO(Oiso-C₅H₁₁)Cl₂, VO(Oiso-C₅H₁₁)₃, VO(OC₆H₁₃)Cl₂, VO(OC₆H₁₃)₁.₅Cl₁.₅, VO(OC₆H₁₃)₂Cl, VO(OC₆H₁₃)₃, VO(OC₈H₁₇)₂Cl, VO(OC₈H₁₇)₁.₅Cl₁.₅, VO(OC₈H₁₇)Cl₂, VO(OC₈H₁₇)₃, VO(OC₁₀H₂₁)Cl₂, VO(OC₁₀H₂₁)₁.₅Cl₁.₅, VO(OC₁₀H₂₁)₂Cl, VO(OC₁₀H₂₁)₃, VO(OC₁₂H₂₅)Cl₂, VO(OC₁₂H₂₅)₁.₅Cl₁.₅, VO(OC₁₂H₂₅)₂Cl, VO(OC₁₂H₂₅)₃, VO(OC₁₅H₃₁)Cl₂, VO(OC₁₅H₃₁)₁.₅Cl₁.₅, VO(OC₁₅H₃₁)₂Cl, VO(OC₁₅H₃₁)₃, VO(OC₁₈H₃₇)Cl₂, VO(OC₁₈H₃₇)₁.₅Cl₁.₅, VO(OC₁₈H₃₇)₂Cl, VO(OC₁₈H₃₇)₃, VO(OC₂₀H₄₁)Cl₂, VO(O-C₂₀H₄₁)₁.₅Cl₁.₅, VO(OC₂₀H₄₁)₂Cl, VO(OC₂₀H₄₁)₃, VO(OC₂₀H₄₁)Cl₂, VO(OC₂₀H₄₁)₃, and VCl₄.

Among these compounds, VOCl₃, VO(OC₂H₅)Cl₂ and VCl₄ are especially preferred.

The organoaluminum compound used with the vanadium compound may be those which are usually employed in the production of ethylene/alpha-olefin copolymers. Generally, they include compounds of the following formula

$$R^2{}_m AlX^2{}_{3-m} \qquad (II)$$

wherein $R^2$ represents an aliphatic hydro-carbon group having 1 to 6 carbon atoms, preferably 2 to 4 carbon atoms, $X^2$ represents a halogen atom, and m is a number of 1 to 3.

The aliphatic hydrocarbon group $R^2$ and the halogen $X^2$ in formula (II) may be $R^1$ and $X^1$ in formulae (I-a) and (I-b).

Specific examples of the organoaluminum compounds include trialkyl aluminums such as $(C_2H_5)_3Al$, (iso-$C_3H_7)_3Al$ and (iso-$C_4H_9)_3Al$, dialkyl aluminum halides such as $(C_2H_5)_2AlCl$, $(C_2H_5)_2AlBr$ and (iso-$C_4H_9)_2AlCl$, alkyl aluminum sesquihalides such as $(C_2H_5)_{1.5}AlCl_{1.5}$, $(C_2H_5)_{1.5}AlBr_{1.5}$ and (iso-$C_4H_9)_{1.5}$—$AlCl_{1.5}$, alkyl aluminum dihalides such as $(C_2H_5)AlCl_2$, (iso-$C_3H_7)AlCl_2$ and (iso-$C_4H_9)AlCl_2$, and mixtures of these in arbitrary proportions.

According to the process of this invention, the copolymerization is carried out in a continuous manner by continuously feeding the catalyst components, ethylene, an alpha-olefin, hydrogen and optionally, an inert medium to the polymerization system (polymerization reactor), and withdrawing the polymer solution substantially continuously from the polymerization system.

The copolymerization is carried out in the liquid phase. The polymerization medium is preferably a liquid medium inert to the polymerization reaction. The alpha-olefin may be used in excess to cause it to serve also as the polymerization medium. Examples of the inert liquid medium used for this purpose include aliphatic hydrocarbons such as butane, pentane, hexane, heptane, octane, decane, dodecane and kerosene; alicyclic hydrocarbons such as cyclopentane, methylcyclopentane, cyclohexane and methylcyclohexane; aromatic hydrocarbons such as benzene, toluene, xylene, and ethylbenzene; and mixtures of these.

In performing the process of this invention, the concentration of the vanadium compound in the polymerization system and the manner of supplying the vanadium compound to the polymerization system are also important factors. The concentration of the vanadium compound in the polymerization system is adjusted to 0.3 millimole to 30 millimoles, preferably 0.5 to 20 millimoles, per liter of the liquid phase. If the concentration of the vanadium compound is below the specified lower limit, the partial pressures of ethylene and the alpha-olefin cannot be so much lowered in order not to reduce the yield of the copolymer per unit amount of the polymerization solvent. Consequently, very high partial pressures of hydrogen are required in order to obtain copolymers of a low molecular weight, and this is disadvantageous both in equipment and operation. If the partial pressure of ethylene or the alpha-olefin is lowered in order to avoid high hydrogen pressures, a copolymer having a low molecular weight can be produced under relatively low pressures, but the yield of the copolymer per unit weight of the polymerization solvent is low. Hence, a huge polymerization apparatus is required, and the cost of separating the copolymer increases. The above defects can be eliminated by maintaining the concentration of the vanadium compound within the above range in the polymerization system, and a copolymer having a low molecular weight can be produced in a high yield per unit amount of the reaction solvent despite the relatively low hydrogen pressure.

The vanadium compound is supplied to the polymerization system as a solution in a polymerization medium, preferably an inert liquid medium. The vanadium compound should not be fed in a much higher concentration than that in the polymerization system as in the production of a high-molecular-weight copolymer. The concentration of the vanadium compound in the solution should be 1 to 5 times, preferably 1 to 4 times, the concentration of the vanadium compound present in the liquid phase of the polymerization system. If the concentration of the vanadium compound in the liquid phase exceeds 5 millimoles/liter, it is especially preferred to feed it in a concentration which is not more than 3 times the concentration of the vanadium compound in the liquid phase. If the vanadium compound is fed into the polymerization system in a concentrated form without the aforesaid dilution, a copolymer which is uniform and has a narrow molecular weight distribution is difficult to obtain.

The amount of the organoaluminum compound is such that the Al/V atomic ratio in the liquid phase of the polymerization system is from 2 to 50, preferably from 3 to 20. Desirably, the organoaluminum compound is to be fed to the polymerization system as a solution or dispersion in a polymerization medium, preferably an inert liquid medium, as in the case of the vanadium compound. Unlike the vanadium compound, the concentration of the organoaluminum compound needs not to be strictly adjusted. For example, the concentration of the organoaluminum is adjusted to not more than 50 times the concentration of the organoaluminum compound present in the polymerization system.

The alpha-olefin to be copolymerized with ethylene in the present invention preferably includes those having 3 to 20 carbon atoms, such as propylene, 1-butene, 1-pentene, 1-hexene, 1-octene, 1-decene, 1-dodecene, 1-tetradecene, 1-octadecene, 1-eicosene, and 4-methyl-1-pentene. They may be used either singly or as a mixture of two or more. Alpha-olefins having 3 to 14 carbon atoms, such as propylene, 1-butene, 1-hexene, 1-octene, 1-decene and 1-dodecene, are especially preferred.

The proportions of the ethylene and the alpha-olefin to be fed to the polymerization system vary depending upon the type of the alpha-olefin or the polymerization conditions, and cannot be generalized. They are adjusted so that the ethylene content of the resulting copolymer is from 30 to 90 mole %, preferably from 35 to 85 mole %. For example, the mole ratio of ethylene to the alpha-olefin is maintained at from 10:1 to 1:10, preferably from 10:2 to 2:10.

The amount of hydrogen used to control the molecular weight of the resulting copolymer also varies depending upon the polymerization conditions. In order to obtain a copolymer having a molecular weight of 300 to 30,000, preferably from 500 to 25,000, the mole ratio of hydrogen to ethylene+alpha-olefin is advantageously adjusted to from 1:100 to 100:1, preferably from 5:100 to 100:5.

The copolymerization temperature is not critical, but is generally 0 to 100° C., preferably 20 to 80° C. The polymerization pressure differs depending upon the polymerization temperature; generally, it is from 0 to 50 kg/cm² (gauge), preferably 0 to 30 kg/cm² (gauge). The average residence time of the polymerization mixture in the polymerization system is from 5 to 300 minutes, preferably 10 to 250 minutes. The polymerization can be stopped by adding an alcohol, etc. in a customary manner to the polymer solution continuously withdrawn after the reaction. The desired copolymer of ethylene and alpha-olefin is separated from the resulting polymer solution in a customary manner by, for example, washing the polymer solution with water to remove the catalyst residue, and then distilling it to remove the polymerization solvent.

The ethylene/alpha-olefin copolymer of the invention so produced is a low-molecular-weight copolymer having an ethylene content of 30 to 90 mole %, preferably 35 to 85 mole %, and a number average molecular weight of from 300 to 30,000, preferably from 500 to 25,000.

The ethylene content of the copolymer, throughout the present specification and claims, is a value measured by $^{13}$C-NMR spectroscopy.

The ethylene/alpha-olefin copolymer provided by this invention is characteristic in that it has a very narrow statistical molecular weight distribution. The statistical molecular weight distribution, as referred to herein, denotes a logarithmic normal distribution, or a distribution similar to it, of molecular weight of the copolymer obtained directly by polymerization from which a substantial amount, for example at least 10% by weight, of a low-molecular-weight component (and/or a high-molecular-weight component) has not yet been removed. This molecular weight distribution is defined by a Q value which is the ratio of the weight average molecular weight to the number average molecular weight and a Z value which is the ratio of the maximum value of the molecular weight to the minimum value of the molecular weight when the molecular weight is measured by gel permeation chromatography. The ethylene/alpha-olefin copolymer provided by this invention has a Q value of not more than 3, preferably not more than 2.8, more preferably not more than 2.6, and a Z value of from 15 to 200, preferably from 20 to 190, more preferably from 30 to 180.

The number average molecular weight and weight average molecular weight of the copolymer are measured by the following method. For details of the method, reference may be made to Journal of Polymer Science, Part A-II, vol. 8, pages 89–103 (1970).

Elution counts of a standard substance having a known molecular weight (16 samples of monodisperse polystyrene having different molecular weights selected from the range of 500 to 840×10⁴) were measured by GPC (gel-permeation chromatography), and a calibration curve showing the relation between the molecular weight and the elution count was prepared. The GPC pattern of a copolymer sample was taken by GPC. From the calibration curve, the molecular weights (Mi) at the individual counts (i) were read, and from the PGC pattern, the elution volumes (Ni) at the individual counts (i) were read. The number average molecular weight ($\overline{M}_n$) and weight average molecular weight ($\overline{M}_w$), both as polystyrene, of the copolymer sample were calculated in accordance with the following equations.

$$\overline{M}_n = \Sigma M i N i / \Sigma N i$$

$$\overline{M}_w = \Sigma M i^2 N i / \Sigma M i N i$$

Separately, the molecular weight, calculated as polystyrene, of squalane (an isoparaffinic standard substance having a molecular weight of 422) was measured by GPC.

Thus, the $\overline{M}_n$, Q value and Z value of the copolymer of this invention were calculated by the following equations.

$$\overline{M}_n \text{ of the copolymer} = \frac{\overline{M}_n \text{ of copolymer as polystyrene}}{\text{Molecular weight of squalane as polystyrene}} \times \text{molecular weight of squalane (422)}$$

$$Q \text{ value} = \frac{\overline{M}_w \text{ of copolymer as polystyrene}}{\overline{M}_n \text{ of copolymer as polystyrene}}$$

The minimum and maximum elution counts of the GPC pattern of the copolymer were read, and the corresponding minimum and maximum molecular weights of the copolymer, calculated as polystyrene, were read from the calibration curve. The Z value was thus calculated from the following equation.

$$Z \text{ value} = \frac{\text{Maximum molecular weight of the copolymer as polystyrene}}{\text{Minimum molecular weight of the copolymer as polystyrene}}$$

The ethylene/alpha-olefin copolymer provided by this invention is useful in various applications according to its inherent properties, especially as a synthetic lubricant, a fuel oil additive or a lubricant oil additive.

For example, copolymers of this invention having an ethylene content of 30 to 70 mole %, preferably 40 to 60 mole %, and a number average molecular weight of 300 to 2,000, preferably 500 to 1,800, can be advantageously used as synthetic lubricant oils.

Thus, the present invention also provides a synthetic lubricant oil consisting substantially of a copolymer of ethylene and an alpha-olefin having an ethylene content of from 30 to 70 mole %, a number average molecular weight of from 300 to 2,000, and a molecular distribution defined by a Q value (the ratio of the weight average molecular weight to the number average molecular weight) of not more than 3 and a Z value (the ratio of the maximum value of the molecular weight to the minimum value of the molecular weight when the molecular weight is measured by gel-permeation chromatography) of from 15 to 200.

In the synthetic lubricant oil of this invention, the copolymer preferably has an ethylene content of at least 30 mole % because such a copolymer has a high viscosity index. In order to obtain good flowability of low temperatures, the ethylene content of the copolymer is preferably up to 70 mole %.

When the copolymer of the invention is intended for use as a synthetic lubricant oil, alpha-olefins having 3 to 14 carbon atoms are preferred for copolymerization with ethylene. In particular, lube oils consisting of ethylene/alpha-olefin copolymers containing alpha-olefins having 8 to 14 carbon atoms as a constituent unit have excellent viscosity characteristics at low temperatures.

Preferably, the ethylene/alpha-olefin copolymer used in the synthetic lubricant oil of the invention has a number average molecular weight of at least 300 in order to obtain a high flash point and not more than 2,000 in order to obtain good flowability.

For use as a lubricant oil, the copolymer may show a statistic molecular weight distribution defined by a Q value of not more than 3, preferably not more than 2.8, and a Z value of 15 to 200, preferably 20 to 190. If the copolymer has a Q value exceeding 3 at the same molecular weight, it has the defect of possessing a lower flash point and a higher pour point. In order for the copolymer to have a good viscosity index in spite of its low Q value, it is important that the copolymer should have a Z value of 15 to 200, thus showing a statistic molecular weight distribution. For example, a copolymer having a Q value of not more than 3 and a molecular weight distribution curve being nearly perpendicular on the low molecular weight side and the high molecular weight side (i.e., having a Z value of not more than 15) which is obtained by subjecting a copolymer having a large Q value to precise distillation is not preferred because it has a low viscosity index.

The synthetic lubricant oil of this invention has a viscosity index of generally at least 130, preferably at least 140, and a kinematic viscosity at 100° C. of usually 4 to 200 centistokes. Even when the lubricant oil of this invention has a kinematic viscosity at 100° C. of more than 60 centistokes, its flowability at low temperatures is good, and it can be suitably used as a lube oil for high loads.

The synthetic lubricant oil of this invention has an flash point of at least 200° C.

As stated above, the synthetic lubricant oil of this invention has the advantage of possessing a high viscosity index, excellent oxidation stability, shear stability and heat stability and high oil film strength. In addition, it is characterized by the fact that despite its high viscosity index, it has a high flash point and low pour point.

Furthermore, since the copolymer of the invention has the aforesaid properties, it is possible to provide not only a practical synthetic lubricant oil of high viscosity for high loads but also a synthetic lubricant oil having a relatively low viscosity at low temperatures.

The synthetic lubricant oil of the invention consists essentially of the copolymer having the aforesaid properties. If required, it may contain an antioxidant, an extreme pressure agent, a cleaning dispersant, etc. and if especially desired, a flowability improver, a viscosity index improver, and other conventional additives in usual amounts. It may also be used in mixture with another lubricant oil.

Ethylene/alpha-olefin copolymers provided by this invention which have an ethylene content of 70 to 90 mole %, preferably 75 to 85 mole %, especially preferably 77 to 83 mole %, and a number average molecular weight of 1,000 to 20,000, preferably 2,000 to 20,000, especially preferably 3,000 to 10,000, can be used advantageously as a fuel oil additive.

It is known that in a cold climate, distillation fuel oils generally have the problem of poor flowability in pipe lines or filters because paraffins contained therein solidify, and in order to improve their flowability, various additives are incorporated. An ethylene/vinyl acetate copolymer (EVA) is a typical example of such an additive. The ethylene/alpha-olefin copolymer of this invention is characterized by the fact that it has excellent solubility in various fuel oils and does not precipitate over long periods of time, and moreover, it improves the low temperature flowability of fuel oils, particularly the cold filter plugging point (C.F.P.P.) (described in Journal of Petroleum, Vol. 52, No. 510) of relatively heavy fuel oils.

The ethylene/alpha-olefin copolymer to be added to a fuel oil is a copolymer of ethylene and an alpha-olefin having an ethylene content of from 70 to 90 mole %, a number average molecular weight of from 1,000 to 20,000, and a molecular weight distribution defined by a Q value (the ratio of the weight average molecular, weight to the number average molecular weight) of not more than 3, preferably not more than 2.8, and a Z value (the ratio of the maximum value of the molecular weight to the minimum value of the molecular, weight when the molecular weight is measured by gel permeation chromatography) of from 15 to 200.

Especially preferably for addition to a fuel oil, the above copolymer has an ethylene content of 75 to 85 mole % and a number average molecular weight of 2,000 to 20,000.

In order to obtain an effect of imparting excellent low-temperature flowability to fuel oils, it is especially preferred that the copolymer have an ethylene content of at least 70 mole % and a number average molecular weight of 1,000 to 20,000.

It is also essential to use copolymers having a Q value of not more than 3 because if the Q value is above 3, the copolymer does not dissolve uniformly in a fuel oil and partly precipitates.

Examples of fuel oils to which the copolymer of the invention is added are straight run or cracked gas oil or a blend in any proportion of straight run and thermally and/or catalytic cracked distillates etc. By uses, such fuel oils include jet fuels, kerosene, heating oils, diesel fuels, etc.

The fuel oil additive composed of the copolymer of this invention exhibits its best effect when added to middle distillate fuel oil having a boiling range of 170 to 400° C. and an end point of at least 360° C.

Preferably, in the fuel oil composition in accordance with this invention, the amount of the ethylene/alpha-olefin copolymer is 0.005 to 5.0% by weight, preferably 0.01 to 1.0% by weight, based on the weight of the fuel oil.

Ethylene/alpha-olefin copolymers of this invention which have an ethylene content of 50 to 90 mole %, preferably 50 to 80 mole %, and a number average molecular weight of 5000 to 25000 are also effectively used as lubricant oil additives.

In addition to the aforesaid uses, the ethylene/alpha-olefin copolymers of the invention having excellent uniformity can also be used as base oils of greases, textile finishing oils heat transfer medium oils, and the like.

The following examples illustrate the present invention more specifically.

EXAMPLE 1

An ethylene/propylene copolymer was synthesized continuously by using a 4-liter glass reactor equipped with stirring impellers.

2 liters of hexane as a solvent, 1 liter of a hexane solution of vanadyl trichloride (16 millimoles/liter), and 1 liter of a hexane solution (96 millimoles/liter) of ethyl aluminum sesquichloride were fed hourly into the reactor from its top in a continuous manner. In the meantime, the reaction solution was continuously withdrawn from the bottom of the reactor so that the amount of the reaction solution in the reactor was always kept at 2 liters. A gaseous mixture of ethylene, propylene and hydrogen (50 liters/hr of ethylene, 62 liters/hr of propylene and 188 liters/hr of hydrogen) was fed into the reactor from its top.) The reaction temperature was adjusted to 35 ° C. by circulating hot water through a jacket mounted on the outside of the reactor. A small amount of methanol was added to the reaction solution withdrawn from the bottom of the reactor to stop the reaction. Then, the reaction solution was washed with water three times, and then distilled under a reduced pressure of 30 mmHg at a pot temperature of 100° C. to remove the hexane solvent. There was obtained an ethylene/propylene copolymer having the properties shown in Table 1.

EXAMPLE 2

The procedure of Example 1 was followed except that a 20 millimoles/liter hexane solution of vanadyl trichloride, a 240 millimoles/liter hexane solution of ethyl aluminum sesquichloride and hexane were fed respectively at a rate of 2 liters/hr, 1 liters/hr and 1 liters/hr. There was obtained an ethylene/propylene copolymer having the properties shown in Table 1.

EXAMPLE 3

The procedure of Example 1 was followed except that the amounts of ethylene, propylene and hydrogen fed were changed respectively to 62 liters/hr, 42 liters/hr, and 195 liters/hr. There was obtained an ethylene/propylene copolymer having the properties shown in Table 1.

EXAMPLE 4

The procedure of Example 1 was followed except that vanadium tetrachloride was used instead of vanadyl trichloride. There was obtained an ethylene/propylene copolymer having the properties shown in Table 1.

EXAMPLE 5

The procedure of Example 1 was followed except that vanadyl ethoxydichloride ($VO(OC_2H_5)Cl_2$) was used instead of vanadyl trichloride. There was obtained an ethylene/propylene copolymer having the properties shown in Table 1.

EXAMPLE 6

The procedure of Example 1 was followed except that the amounts of ethylene, hydrogen and hexane solvent fed were changed respectively to 30 liters/hr, 180 liters/hr and 1 liter/hr, and 1 liter/hr of a hexane solution (340 g/liter) of hexene-1 was used instead of propylene. There was obtained an ethylene/hexene-1 copolymer having the properties shown in Table 1.

EXAMPLE 7

The procedure of Example 1 was followed except that the amounts of ethylene, hydrogen and hexane solvent were changed respectively to 36 liters/hr, 180 liters/hr and 1 liter/hr, and 1 liter/hr of decene-1 was used instead of propylene. There was obtained an ethylene/decene-1 copolymer having the properties shown in Table 1.

COMPARATIVE EXAMPLE 1

The procedure of Example 1 was followed except that a 160 millimoles/liter hexane solution of vanadyl trichloride as the vanadium compound and the hexane solvent were fed respectively at a rate of 0.1 liters/hr and 2.9 liters/hr. There was obtained an ethylene-propylene copolymer having the properties shown in Table 1.

COMPARATIVE EXAMPLE 1'

The copolymer obtained in Comparative Example 1 was dewaxed with methyl ethyl ketone in accordance with the method described in "Lubricant Oils and Greases" written by Hiroshi Horiguchi, and then subjected to topping under a reduced pressure of 0.1 mmHg at a pot temperature of 200° C. The resulting product oil had the properties shown in Table 1.

COMPARATIVE EXAMPLE 2

The procedure of Example 1 was followed except that 100 millimoles/liter hexane solution of vanadyl trichloride as the vanadium compound and the hexane solvent were fed respectively at a rate of 0.4 liter/hr and 2.6 liters/hr. There was obtained an ethylene/propylene copolymer having the properties shown in Table 1.

COMPARATIVE EXAMPLE 3

The procedure of Example 1 was followed except that the amounts of ethylene, propylene and hydrogen fed were changed respectively to 5 liters/hr, 100 liters/hr and 195 liters/hr. There was obtained an ethylene/propylene copolymer having the properties shown in Table 1.

COMPARATIVE EXAMPLE 4

The procedure of Example 1 was followed except that the amounts of ethylene, propylene and hydrogen fed were changed respectively to 21 liters/hr, 24 liters/hr and 225 liters/hr. There was obtained an ethylene/propylene copolymer having the properties shown in Table 1.

COMPARATIVE EXAMPLE 5

An ethylene/propylene copolymer was synthesized by a batchwise method in a 2-liter glass reactor equipped with stirring impellers.

In the reactor, a hexane solution of ethyl aluminum sesquichloride (24 millimoles/0.75 liter) was prepared. From the top of the reactor, a hexane solution of vanadyl trichloride (4 millimoles/0.75 liter) was added dropwise through a dropping funnel. Simultaneously, a gaseous mixture of ethylene, propylene and hydrogen (50 liters/hr of ethylene, 62 liters/hr of propylene and 188 liters/hr of hydrogen) was fed into the reactor, and the reaction was started. The reaction temperature was adjusted to 35° C. by an ice water bath and a warm water bath. Thirty minutes after the start of the reaction, a small amount of methanol was added to the reaction mixture from the top of the reactor to stop the reaction. The reaction mixture was then worked up in the same way as in Example 1. There was obtained an ethylene/propylene copolymer having the properties shown in Table 1.

TABLE 1

| | Concentration of the vanadium catalyst (millimoles/l) | Ethylene content (mole %) | Number average molecular weight ($\overline{M_n}$) | Q Value | Z Value | Pour point (°C.) (*1) | Kinematic viscosity at 100° C. (cst) (*2) | Viscosity index (*3) | Flash point (°C.) (*4) | Appearance of the copolymer |
|---|---|---|---|---|---|---|---|---|---|---|
| Example | | | | | | | | | | |
| 1 | 4 | 52 | 960 | 2.6 | 110 | −37.5 | 60.6 | 175 | 265 | Colorless and clear |
| 2 | 10 | 51 | 750 | 2.1 | 80 | −42.5 | 23.5 | 160 | 240 | Colorless and clear |
| 3 | 4 | 64 | 880 | 1.8 | 80 | −37.5 | 36.6 | 175 | 260 | Colorless and clear |
| 4 | 4 | 53 | 940 | 2.5 | 105 | −37.5 | 58.3 | 175 | 260 | Colorless and clear |
| 5 | 4 | 51 | 950 | 2.6 | 110 | −37.5 | 60.3 | 175 | 260 | Colorless and clear |
| 6 | 4 | 57 | 910 | 2.2 | 110 | −37.5 | 34.7 | 140 | 240 | Colorless and clear |
| 7 | 4 | 44 | 1100 | 2.2 | 100 | −47.5 | 33.5 | 172 | 265 | Colorless and clear |
| Comparative Example | | | | | | | | | | |
| 1 | 4 | 53 | 970 | 3.6 | 370 | −25.0 | 90.3 | 175 | 195 | Opalescent |
| 1' | 4 | 51 | 950 | 2.1 | 10 | −35.0 | 62.5 | 155 | 260 | Colorless and clear |
| 2 | 10 | 52 | 890 | 3.8 | 450 | −27.5 | 41.2 | 170 | 190 | Opalescent |
| 3 | 4 | 10 | 810 | 2.5 | 100 | −27.5 | 29.3 | 66 | 230 | Colorless and clear |
| 4 | 4 | 55 | 250 | 2.6 | 30 | −60 | 2.3 | 165 | 120 | Colorless and clear |
| 6 | 5 | 55 | 930 | 9.3 | 870 | +100 | Impossible of measurement | Impossible of measurement | — | Mixture of a white wax and a colorless liquid |

(*1): Measured by JIS K-2269-80;
(*2): Measured by JIS K-2283-80;
(*3): Measured by JIS K-2283-80;
(*4): Measured by JIS K-2265-80.

EXAMPLE 8

The procedure of Example 1 was followed except that the concentration of the hexane solution of vanadyl trichloride was changed to 4 millimoles/liter, the concentration of the hexane solution of ethyl aluminum sesquichloride was changed to 24 millimoles/liter, and the amounts of ethylene, propylene and hydrogen fed were changed respectively to 210 liters/hr, 60 liters/hr and 30 liters/hr. The resulting copolymer had an ethylene content of 78 mole %, an average molecular weight of 8,200, a Q value of 2.1 and a Z value of 170. The polymer was added in a concentration of 5% by weight to a mineral oil (150 neutral oil having a viscosity index of 103). The resulting solution was clear at room temperature and had a viscosity index of 162, good ultrasonic shear stability and a viscosity decrease at 210° F., measured in accordance with ASTM D-203, of 5%.

COMPARATIVE EXAMPLE 6

The procedure of Example 1 was followed except that the concentration of the hexane solution of vanadyl trichloride was changed to 24 millimoles/liter and the amounts of the hexane solvent, ethylene, propylene and hydrogen were changed respectively to 2.9 liters/hr, 210 liters/hr, 60 liters/hr, and 30 liters/hr. The resulting copolymer had an ethylene content of 77 mole %, an average molecular weight of 8,100, a Q value of 3.7, and a Z value of 460. A solution obtained by adding the copolymer in a concentration of 5% by weight to a mineral oil (150 neutral oil having a viscosity index of 103) was opalescent at room temperature and was unsuitable for use as a lubricant oil.

COMPARATIVE EXAMPLE 7

The procedure of Example 1 was followed except that the concentrations of the hexane solution of vanadyl trichloride and the hexane solution of ethyl aluminum sesquichloride were changed respectively to 2.4 millimoles/liter and 14.4 millimoles/liter, and the amounts of ethylene, propylene and hydrogen were changed respectively to 180 liters/hr, 119 liters/hr, and 1 liter/hr. The resulting copolymer had an ethylene content of 64 mole %, an average molecular weight of 50,000, a Q value of 2.4 and a Z value of 170. A solution obtained by adding the copolymer in a concentration of 5% by weight to a mineral oil (150 neutral oil having a viscosity index of 103) had poor ultrasonic shear stability and a viscosity decrease at 210° F. of 20%.

COMPARATIVE EXAMPLE 8

The procedure of Example 1 was followed except that the concentrations of the hexane solution of vanadyl trichloride and the hexane solution of ethyl aluminum sesquichloride were changed respectively to 4 millimoles/liter and 24 milliliters/liter, and the amounts of ethylene, propylene and hydrogen were changed respectively to 160 liters/hr, 20 liters/hr, and 120 liters/hr. The resulting copolymer had an ethylene content of 93 mole %, an average molecular weight of 5,400, a Q value of 2.3 and a Z value of 165. The resulting copolymer was scarcely soluble in middle distillate fuel (I) (initial boiling point 225° C.; end point 374° C.; pour point (P.P.) 2.5° C.; cold filter plugging point (C.F.P.P.) 2° C.) at room temperature.

COMPARATIVE EXAMPLE 9

The procedure of Example 1 was followed except that the concentration of the hexane solution of vanadyl trichloride was changed to 40 millimoles/liter and it was fed at a rate of 0.1 liter/hr; the concentration of the hexane solution of ethyl aluminum sesquichloride was changed to 24 millimoles/liter; and the amounts of the hexane solvent, ethylene, propylene and hydrogen were changed respectively to 2.9 liters/hr, 148 liters/hr, 32 liters/hr and 120 liters/hr. The resulting copolymer had an ethylene content of 82 mole %, an average molecular weight of 5,300, a Q value of 3.8, and a Z value of 420. A solution obtained by adding this polymer in a concentration of 0.05% by weight of middle distillate fuel (I) (initial boiling point 225° C.; end point 374° C.; pour point (P.P.) 2.5° C.; cold filter plugging point (C.F.P.P.) 2° C.) was opalescent at room temperature, and had a pour point of 2° C.

EXAMPLE 9

An ethylene/propylene copolymer was synthesized continuously by using a 4-liter glass reactor equipped with stirring impellers.

Two liters of hexane as a solvent, 1 liter of a hexane solution of vanadyl trichloride (16 millimoles/liter) and 1 liter of a hexane solution of ethyl aluminum sesquichloride (96 millimoles/liter) were continuously fed hourly into the reactor from its top. In the meantime, the reaction solution was continuously withdrawn from the bottom of the reactor so that the amount of the reaction solution in the reactor was always kept at 2 liters (the concentration of vanadyl trichloride in the reaction: 4 millimoles/liter). A gaseous mixture of ethylene, propylene and hydrogen (90 liters/hr of ethylene, 90 liters/hr of propylene and 120 liter/hr of hydrogen) was introduced into the reactor from its top. The reaction temperature was adjusted to 35° C. by circulating hot water through a jacket mounted on the outside of the reactor. A small amount of methanol was added to the reaction solution withdrawn from the bottom of the reactor to stop the reaction. The reaction solution was then washed with water three times, and then distilled under a reduced pressure of 30 mmHg at a pot temperature of 100° C. to remove the hexane solvent. There was obtained an ethylene/propylene copolymer having the properties shown in Table 2.

EXAMPLE 10

The procedure of Example 9 was followed except that the amounts of ethylene, propylene and hydrogen fed were changed respectively to 70 liters/hr, 70 liters/hr and 160 liters/hr. There was obtained an ethylene/propylene copolymer having the properties shown in Table 2.

EXAMPLE 11

The procedure of Example 9 was followed except that the amounts of ethylene, propylene and hydrogen were changed respectively to 53 liters/hr, 52 liters/hr, and 195 liters/hr. There was obtained an ethylene/propylene copolymer having the properties shown in Table 2.

EXAMPLE 12

The procedure of Example 9 was followed except that the amounts of ethylene, propylene and hydrogen fed were changed respectively to 50 liters/hr, 48 liters/hr and 202 liters/hr. There was obtained an ethylene/propylene copolymer having the properties shown in Table 2.

EXAMPLE 13

The procedure of Example 9 was followed except that the amounts of ethylene, propylene and hydrogen fed were changed respectively to 46 liters/hr, 44 liters/hr and 210 liters/hr. There was obtained an ethylene/propylene copolymer having the properties shown in Table 2.

EXAMPLE 14

The procedure of Example 9 was followed except that the amounts of ethylene, propylene and hydrogen were changed respectively to 35 liters/hr, 55 liters/hr and 210 liters/hr. There was obtained an ethylene/propylene copolymer having the properties shown in Table 2.

EXAMPLE 15

The procedure of Example 9 was followed except that the amounts of ethylene, propylene and hydrogen were changed respectively to 55 liters/hr, 35 liters/hr and 210 liters/hr. There was obtained an ethylene/propylene copolymer having the properties shown in Table 2.

EXAMPLE 16

The procedure of Example 9 was followed except that the amounts of ethylene and hydrogen were changed respectively to 10 liters/hr and 270 liters/hr; instead of propylene, an n-decane solution (0.5 liters/liter of n-decane) of decene-1 was fed at a rate of 1 liter/hr instead of propylene; vanadyl trichloride and ethyl aluminum sesquichloride were fed as n-decane solutions; and that the reaction temperature was adjusted to 50° C. There was obtained an ethylene/decene-1 copolymer having the properties shown in Table 2.

COMPARATIVE EXAMPLE 10

The copolymer obtained in Comparative Example 5 was distilled under a reduced pressure of 0.06 mmHg in a rectifying column, and fractions obtained at an overhead temperature of 160 to 280° C. were collected as a product oil. The GPC chart of the product oil showed a non-statistic molecular weight distribution. The properties of the product oil are also shown in Table 2.

COMPARATIVE EXAMPLE 11

The procedure of Example 9 was followed except that the amounts of ethylene, propylene and hydrogen were changed respectively to 18 liters/hr, 22 liters/hr and 260 liters/hr. There was obtained an ethylene/propylene copolymer having the properties shown in Table 2.

COMPARATIVE EXAMPLE 12

The procedure of Example 9 was followed except that ethylene, propylene and hydrogen were changed respectively to 105 liters/hr, 105 liters/hr and 90 liters/hr. There was obtained an ethylene/propylene copolymer having the properties shown in Table 2.

COMPARATIVE EXAMPLE 13

The procedure of Example 9 was repeated except that the amounts of ethylene, propylene and hydrogen were changed respectively to 73 liters/hr, 32 liters/hr and 195 liters/hr.

There was obtained an ethylene/propylene copolymer having the properties shown in Table 2.

COMPARATIVE EXAMPLE 14

The procedure of Example 9 was followed except that the amounts of ethylene, propylene and hydrogen were changed respectively to 5 liters/hr, 100 liters/hr and 195 liters/hr. There was obtained an ethylene/propylene copolymer having the properties shown in Table 2.

and the hexane solution of diethyl aluminum sesquichloride were changed respectively to 20 and 160 millimoles/liter, and the amounts of ethylene, propylene and hydrogen fed were changed respectively to 200 liters/hr, 40 liters/hr, and 60 liters/hr. The resulting ethylene/propylene copolymer had an ethylene content of 83 mole %, a number average molecular weight of 3,300, a Q value of 2.4, and a Z value of 160.

The resulting copolymer was added in a proportion of 0.05%, by weight to the same middle distillate fuel (I) as

TABLE 2

| | Ethylene content (mole %) | Average molecular weight ($\overline{M}_n$) | Q value | Z value | Flash point (° C.) (*1) | Pour point (° C.) (*2) | Kinematic viscosity at 100° C. (cst) (*3) | Viscosity at −18° C. (cp) (*4) | Viscosity index ($VI_E$) (*5) | Extreme pressure properties (Four-ball method) (kg/cm$^2$) (*6) |
|---|---|---|---|---|---|---|---|---|---|---|
| Example | | | | | | | | | | |
| 9 | 54 | 1500 | 2.5 | 175 | 286 | −27.5 | 163 | —(*7) | 191 | 9.0 |
| 10 | 55 | 1200 | 2.5 | 170 | 272 | −30.0 | 108 | — | 183 | 8.0 |
| 11 | 53 | 990 | 2.5 | 110 | 263 | −35.0 | 49.6 | — | 171 | 8.0 |
| 12 | 55 | 830 | 2.5 | 90 | 260 | −45.0 | 21.3 | — | 167 | 6.0 |
| 13 | 55 | 550 | 2.3 | 30 | 235 | −55.0 | 7.00 | — | 163 | 5.5 |
| 14 | 41 | 540 | 2.4 | 30 | 232 | −55.0 | 6.82 | — | 160 | 5.5 |
| 15 | 62 | 550 | 2.4 | 30 | 236 | −52.5 | 7.06 | 900 | 166 | 5.5 |
| 16 | 46 | 580 | 2.1 | 50 | 241 | −50.0 | 7.80 | 760 | 163 | 6.0 |
| Comparative Example | | | | | | | | | | |
| 10 | 55 | 560 | 1.1 | 10 | 237 | −37.5 | 6.46 | 2000 | 121 | 5.0 |
| 11 | 53 | 200 | 2.3 | 30 | 98 | below −60° C. | 2.31 | — | 161 | 2.5 |
| 12 | 54 | 3100 | 2.5 | 170 | 292 | +10.0 | — | — | — | 7.0 |
| 13 | 72 | 830 | 2.5 | 80 | 260 | +5.0 | 46.6 | — | 170 | 5.0 |
| 14 | 10 | 810 | 2.5 | 75 | 230 | −27.5 | 29.3 | — | 66 | 4.0 |

(*1): Measured by JIS K-2265-80;
(*2): Measured by JIS K-2269-80;
(*3): Measured by JIS K-2283-80;
(*4): Measured by JIS K-2215-80;
(*5): Measured by JIS K-2283-80;
(*6): Measured by JIS K-2519-59;
(*7): The symbol "—" indicates that no measurement was made.

EXAMPLE 17

The procedure of Example 1 was followed except that the concentrations of the hexane solution of vanadyl trichloride and the hexane solution of ethyl aluminum sesquichloride were changed respectively to 4 and 32 millimoles/liter, and the amounts of ethylene, propylene and hydrogen fed were changed respectively to 140 liters/hr, 40 liters/hr and 120 liters/hr. The resulting ethylene/propylene copolymer had an ethylene content of 79 mole %, a number average molecular weight of 4,800, a Q value of 2.5 and a Z value of 170.

The copolymer was added in a proportion of 0.05%, by weight to a middle distillate fuel (I) (initial boiling point 225° C.; end point 374° C.; pour point (P.P.) 2.5° C.; cold filter plugging point (C.F.P.P.) 2° C.). The P.P. and C.F.P.P. of the resulting mixture were found to be −25.0° C. and −7° C., respectively. This shows that the low-temperature flowability of the middle distillate fuel (I) was considerably improved by the addition of the copolymer.

The P.P. was measured in accordance with JIS K-2269, and C.F.P.P. was measured by the method described in Journal of Petroleum, Vol. 52, N. 510.

EXAMPLE 18

The procedure of Example 1 was followed except that the concentrations of the hexane solution of vanadyl trichloride used in Example 17. The resulting mixture was found to have a P.P. of −20° C. and a C.F.P.P. of −6° C. This shows that the low-temperature flowability of the middle distillate fuel (I) was considerably improved by the addition of the copolymer. The P.P. and C.F.P.P. were measured by the same methods as in Example 19.

EXAMPLE 19

The procedure of Example 1 was followed except that the concentrations of the hexane solution of vanadyl trichloride and the hexane solution of ethyl aluminum sesquichloride were changed respectively to 4 and 32 millimoles/liter, and the amounts of ethylene, propylene and hydrogen fed were changed respectively to 85 liters/hr, 200 liters/hr, and 15 liters/hr. The resulting ethylene propylene copolymer had an ethylene content of 52 mole %, a number average molecular weight of 18,000, a Q value of 2.4 and a Z value of 175.

What we claim is:

1. A copolymer of ethylene and an alpha-olefin having a ethylene content of from 40 to 60 mole %, a number average molecular weight of from 300 to 8,200 and a molecular weight distribution value Q, which is the ratio of the weight average molecular weight to the number average molecular weight, of not more than 3 and a Z value, which is the ratio of the maximum value of the molecular weight to the minimum value of the molecular weight when the molecular weight is measured by gel permeation chromatography, of from 15 to 200 said copolymer being a transparent liquid at 20° C.

2. The copolymer of claim 1 which has a Q value of not more than 2.8.

3. The copolymer of claim 1 which has a Z value of from 20 to 190.

4. The copolymer of claim 1 wherein the alpha-olefin has 3 to 20 carbon atoms.

5. The copolymer of claim 1 wherein the alpha-olefin has 3 to 14 carbon atoms.

6. The copolymer of claim 1 wherein the alpha-olefin is at least one member selected from the group consisting of propylene, butene-1, pentene-1, hexene-1, octene-1, nonene-1, decene-1, undecene-1, dodecene-1, tridecene-1 and tetradecene-1.

7. The copolymer of claim 1 being useful as a synthetic lubricant oil having an ethylene content of from 40 to 60 mole % and a number average molecular weight of from 300 to 2,000.

8. The copolymer of claim 7 which has a viscosity index of at least 130.

9. The synthetic lubricant oil of claim 8 having a kinematic viscosity at 130° C. of from 4 to 200 centistokes.

10. The copolymer of claim 1 wherein the alpha-olefin is hexene-1 or decene-1.

11. A copolymer of ethylene and at least one alpha-olefin having from 3 to 14 carbon atoms, said copolymer having an ethylene content of from 40 to 60 mole percent, a number average molecular weight of from 300 to 8,200, a molecular weight distribution value Q, which is the ratio of the weight average molecular weight to the number average molecular weight, of not more than 2.8, and a Z value, which is the ratio of the maximum value of the molecular weight to the minimum value of the molecular weight, when the molecular weight is measured by gel permeation chromatography, of from 20 to 90 said copolymer being a transparent liquid at 20° C.

12. The copolymer of claim 11 wherein the alpha-olefin is propylene.

13. The copolymer of claim 11 wherein the alpha-olefin has from 8 to 14 carbon atoms.

14. The copolymer of claim 13 wherein the alpha-olefin is decene-1.

15. A synthetic lubricant oil comprising the copolymer of claim 1 having a kinematic viscosity at 100° C. of 4 to 200 centistrokes.

16. A synthetic oil for use as a lubricant oil consisting essentially of the copolymer of claim 1, and having a kinematic viscosity at 100° C. of 4 to 200 centistokes.

17. The copolymer of claim 1 which has a pour point below 0° C.

18. The copolymer of claim 1 which has a pour point of not more than −27.5° C.

19. The copolymer of claim 11 which has a pour point below 0° C.

20. The copolymer of claim 11 which has a pour point of not more than −27.5° C.

* * * * *